(12) United States Patent
Wilmink

(10) Patent No.: US 10,743,811 B2
(45) Date of Patent: Aug. 18, 2020

(54) FALL PREDICTION ASSESSMENT

(71) Applicant: CarePredict, Inc., Plantation, FL (US)

(72) Inventor: Gerald J. Wilmink, San Antonio, TX (US)

(73) Assignee: CarePredict, Inc., Plantation, FL (US)

( * ) Notice: Subject to any disclaimer, the term of this patent is extended or adjusted under 35 U.S.C. 154(b) by 1069 days.

(21) Appl. No.: 14/057,687

(22) Filed: Oct. 18, 2013

(65) Prior Publication Data
US 2015/0112163 A1    Apr. 23, 2015

(51) Int. Cl.
| A61B 5/00 | (2006.01) |
| A61B 5/11 | (2006.01) |
| G16H 40/63 | (2018.01) |
| G16H 50/30 | (2018.01) |
| G16H 10/60 | (2018.01) |

(52) U.S. Cl.
CPC ............ *A61B 5/443* (2013.01); *A61B 5/1117* (2013.01); *A61B 5/7275* (2013.01); *G16H 10/60* (2018.01); *G16H 40/63* (2018.01); *G16H 50/30* (2018.01)

(58) Field of Classification Search
None
See application file for complete search history.

(56) References Cited

U.S. PATENT DOCUMENTS

| 6,966,877 B2 | 11/2005 | Lahtinen |
| 7,242,318 B2 | 7/2007 | Harris |
| 7,733,224 B2 | 6/2010 | Tran |
| 8,182,425 B2 | 5/2012 | Stamatas et al. |
| 2005/0182305 A1* | 8/2005 | Hendrich ............... A61B 5/00 600/300 |
| 2007/0043301 A1 | 2/2007 | Martinsen et al. |
| 2008/0039700 A1* | 2/2008 | Drinan ................. A61B 5/0537 600/301 |
| 2008/0081962 A1 | 4/2008 | Miller et al. |

(Continued)

FOREIGN PATENT DOCUMENTS

| CA | 2514799 A1 | 8/2004 |
| EP | 1 229 824 B1 | 7/2005 |
| EP | 2 387 942 A1 | 11/2011 |

OTHER PUBLICATIONS

Carter, James M., et al. "Hydration status of Arabic adolescents and young men: Measurement, evaluation, and a school-based initiative to improve drinking behaviour." International journal of sport nutrition and exercise metabolism 22.4 (2012): 257-266.*

(Continued)

*Primary Examiner* — Jacqueline Cheng
*Assistant Examiner* — Jairo H Portillo
(74) *Attorney, Agent, or Firm* — DLA Piper LLP (US)

(57) ABSTRACT

Methods, apparatuses, and computer readable mediums for fall prediction assessment are provided. In a particular embodiment, a fall prediction profile generator is configured to identify, based on health status data associated with a patient, a hydration threshold for the patient. The fall prediction profile generator is also configured to store the identified hydration threshold as part of a hydration profile associated with the patient and provide the hydration profile to a fall prediction controller to generate a fall prediction assessment of the patient based on the hydration profile and a current hydration indicator associated with the patient.

17 Claims, 12 Drawing Sheets

(56) References Cited

U.S. PATENT DOCUMENTS

| | | | |
|---|---|---|---|
| 2008/0186189 A1* | 8/2008 | Azzaro | A61B 5/1113 340/573.7 |
| 2008/0275319 A1 | 11/2008 | Van Gogh et al. | |
| 2008/0306362 A1* | 12/2008 | Davis | A61B 5/14521 600/307 |
| 2010/0185064 A1* | 7/2010 | Bandic | A61B 5/0059 600/306 |
| 2010/0261980 A1* | 10/2010 | Peng | G08B 21/0446 600/301 |
| 2011/0184261 A1* | 7/2011 | Menon | A61B 5/4869 600/318 |
| 2011/0230791 A1 | 9/2011 | Ten Kate et al. | |
| 2012/0220835 A1 | 8/2012 | Chung | |
| 2012/0253207 A1* | 10/2012 | Sarkar | A61B 5/0004 600/483 |
| 2013/0066170 A1 | 3/2013 | Mattoli et al. | |
| 2013/0143519 A1* | 6/2013 | Doezema | G08B 21/0446 455/404.2 |
| 2013/0144136 A1* | 6/2013 | Rymut | A61B 5/0059 600/310 |
| 2013/0159418 A1 | 6/2013 | Jung et al. | |
| 2015/0112162 A1 | 4/2015 | Wilmink | |

OTHER PUBLICATIONS

Concannon, Leah G., Matthew J. Grierson, and Mark A. Harrast. "Exercise in the older adult: from the sedentary elderly to the masters athlete." PM&R 4.11 (2012): 833-839.*

Close, J. C., and Stephen R. Lord. "Fall assessment in older people." BMJ 343.d5153 (2011).*

Berry, Sarah D., and Ram R. Miller. "Falls: epidemiology, pathophysiology, and relationship to fracture." Current osteoporosis reports 6.4 (2008): 149-154.*

Lan, M. et al., "SmartFall: An Automatic Fall Detection System Based on Subsequence Matching for the SmartCane", 4th International Conference on Body Area Networks (BodyNets '09), Apr. 2009, The Institute for Computer Sciences, Social Informatics and Telecommunications Engineering (ICST), Los Angeles, California USA.

Armstrong, "Review: Assessing Hydration Status: The Elusive Gold Standard", Journal of the American College of Nutrition, vol. 26, No. 5(S), Oct. 2007, pp. 575S-584S, American College of Nutrition, Clearwater Florida, USA.

Marchand, "Development of a dehydration sensor integrated on fabric", $6^{th}$ International Workshop on Wearable and Implantable Body Sensor Networks, Jun. 2009, IEEE Xplore Digital Library (online), ieee.org, DOI: 10.1109/BSN.2009.29.

\* cited by examiner

FALL PREDICTION ASSESSMENT

BACKGROUND

Field of the Invention

The field of the invention is data processing, or, more specifically, methods, apparatuses, and computer readable mediums for fall prediction assessment.

Description of Related Art

A public health issue of concern is the incidence of falls, in which a patient falls to the ground from an upright position while standing or walking. The effect of a fall on an elderly patient can be particularly serious. In some cases a fall causes the death of a patient, either at the time of the fall or indirectly as a result of the injuries sustained. Even in non-fatal incidences, the injuries suffered from a fall can be devastating to the patient's physical and mental well-being.

SUMMARY

Methods, apparatuses, and computer readable mediums for fall prediction assessment are provided. In a particular embodiment, a fall prediction profile generator is configured to identify, based on health status data associated with a patient, a hydration threshold for the patient. The fall prediction profile generator is also configured to store the identified hydration threshold as part of a hydration profile associated with the patient and provide the hydration profile to a fall prediction controller to generate a fall prediction assessment of the patient based on the hydration profile and a current hydration indicator associated with the patient.

A heath care provider may use a fall prediction assessment to determine when to intervene or provide care for a patient that is identified as at risk of falling. Providing care for a patient before a fall could save the patient from the considerable cost involved in the treatment and hospitalization of fall injuries and even death.

The foregoing and other objects, features and advantages of the present disclosure will become apparent after review of the entire application, including the following sections: Brief Description of the Drawings, Detailed Description, and the Claims.

DETAILED DESCRIPTION

Figure 1:
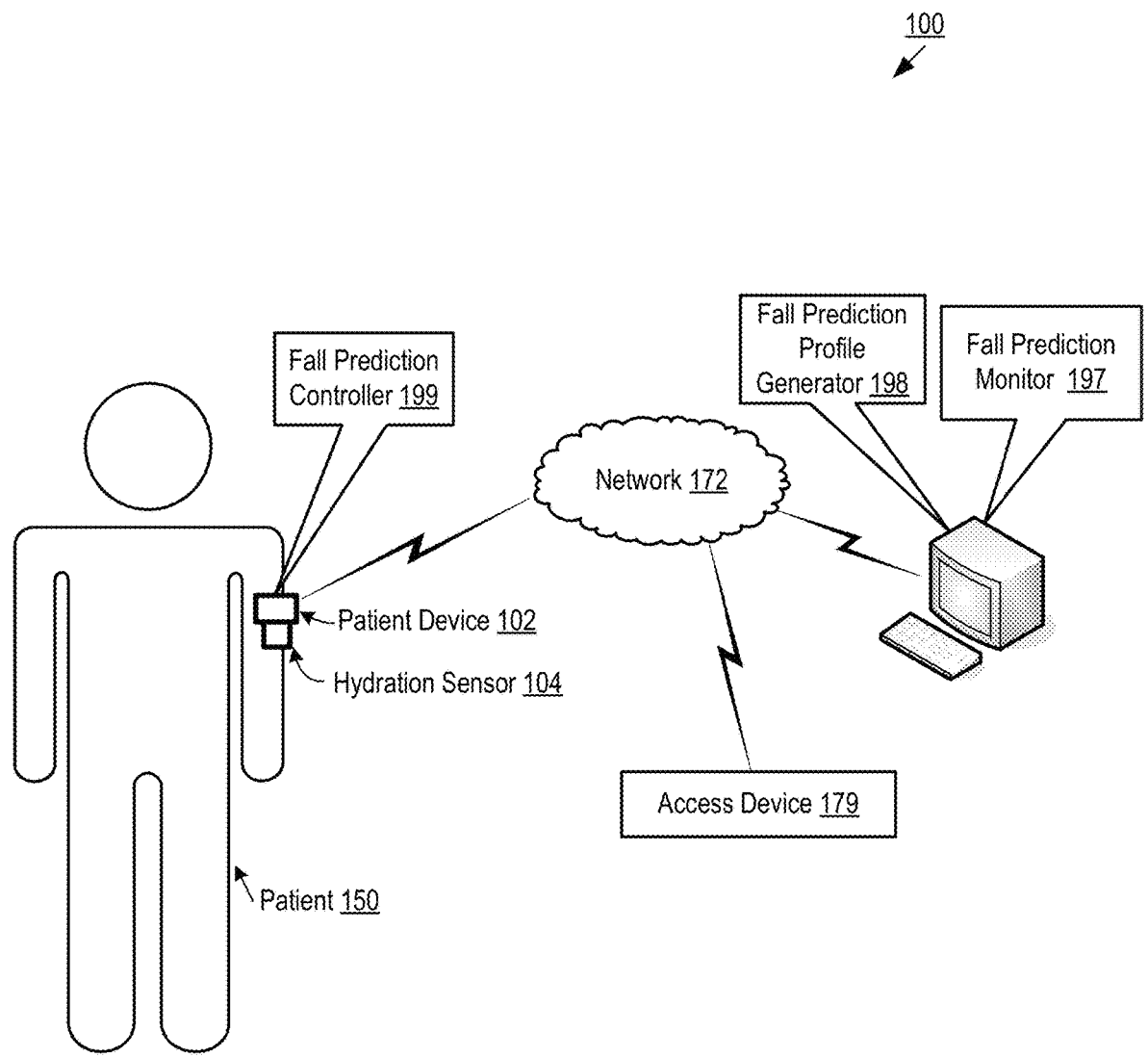
FIG. 1 sets forth a block diagram of an illustrative embodiment of an apparatus that includes a fall prediction controller and a fall prediction profile generator.

Referring to FIG. 1, an illustrative apparatus (100) for fall prediction assessment is shown. The apparatus (100) includes a hydration sensor (104) coupled for data communication to a patient device (102). A hydration sensor may be any type of sensor capable of measuring a hydration level of a person. Measuring a hydration level of a person may be performed by a variety of methods via a variety of systems, including but not limited to measuring transepidermal water loss (TWL) with a skin hydration probe. TWL is defined as the measurement of the quantity of water that passes from inside a body through the epidermal layer (skin) to the surrounding atmosphere via diffusion and evaporation processes.

In the example of FIG. 1, the hydration sensor (104) is attached to a patient (150) and is configured to measure a hydration level of the patient (150) and generate a hydration measurement indicating the measured hydration level. The hydration sensor (104) is also configured to provide the hydration measurement to the patient device (102).

The patient device (102) is comprised of automated computing machinery configured for fall prediction assessment. For example, the patient device (102) may include circuitry for periodically polling or receiving hydration measurements from the hydration sensor (104) by monitoring the existence and strength of a signal from the hydration sensor (104). The patient device (102) may also include circuitry for processing the hydration measurements. For example, the patient device (102) may include data acquisition (DAQ) hardware for conversion of the hydration measurement to another data form, such as a hydration indicator. That is, a hydration indicator corresponds to or is an indicator of a measured hydration level of the patient.

The patient device (102) also includes a fall prediction controller (199) comprising automated computing machinery configured to perform a fall prediction assessment. Specifically, the fall prediction controller (199) is configured to compare a hydration indicator to a hydration threshold. A hydration threshold is one or more data values that correspond to a recommended hydration level for a person. A patient having a hydration level that is below the recommended hydration level may be at an increased risk of falling. Comparing the hydration indicator to the hydration threshold may be carried out by determining whether the hydration indicator is below the one or more data values of the hydration threshold and generating a result that indicates whether the hydration indicator is below the one or more data values of the hydration threshold. In a particular embodiment, the result of the comparison is represented as a data value which indicates a difference between the hydration indicator and the hydration threshold. That is, the result of the comparison may represent a severity of separation between the hydration indicator and the hydration threshold.

The fall prediction controller (199) is also configured to generate, based on a result of the comparison of the hydration indicator to the hydration threshold, a fall prediction assessment of the patient (150). A fall prediction assessment of the patient (150) is an indication of the likelihood that the patient is at risk of falling down, stumbling, or otherwise losing his or her balance. A fall prediction assessment may be a simple binary data value, where a '0' represents 'patient is not at risk of falling' and a '1' represents 'patient is at risk of falling'. The fall prediction assessment may also indicate one or more values with a range of possible values where each value has a different risk level associated with it. As a non-limiting example, a '0' data value for the fall prediction assessment may represent 'patient is at a low risk of falling', a '1' may represent 'patient is at a medium risk of falling', a '2' may represent 'patient is a high risk of falling', and a '3' may represent "patient is at a very high risk of falling".

The fall prediction controller (199) may also be configured to use other indicators besides a hydration indicator to generate a fall prediction assessment. In a particular embodiment, the patient device (102) may also be coupled to a variety of other types of sensors and be configured to generate and process indicators corresponding to the other sensors. Non-limiting examples of other types of sensors include a gait monitoring sensor, a blood pressure sensor, a blood sugar sensor, and an accelerometer. That is, in a particular embodiment, the fall prediction controller uses indicators associated with other types of sensors to generate a fall prediction assessment.

The fall prediction controller (199) may also be configured to provide to another device an instruction to perform a fall aid operation based on the fall prediction assessment. For example, the fall prediction controller (199) may send an instruction to access device (179) to perform a fall aid operation. A fall aid operation may be any type of action that assists in fall prevention, fall detection, or response to a fall of the patient. Non-limiting examples of fall aid operations include unlocking doors to a car, room, house, or building; turning on lights in a room; sounding one or more audible alarms or playing recorded instructions to the patient via a speaker; turning on a room intercom that connects the patient with a personal health care provider, such as a nursing attendant; turning on a video camera that provides current video images of the patient to personal health care provider; and many others as will occur to readers of skill in the art.

The fall prediction controller (199) may also be configured to provide a fall prediction assessment to another device. For example, the fall prediction controller (199) may provide the fall prediction assessment to a management device (106) via a network (172). In a particular embodiment, the fall prediction controller (199) is stored on the management device (106) and is configured to receive hydration measurements or hydration indicators from the patient device (102). In this particular embodiment, generation of the fall prediction assessment occurs remote to the patient and sensor instead of local to both the patient and sensor. That is, readers of skill in the art will realize that the fall prediction controller may be incorporated in a variety of devices, not just devices coupled to a sensor.

In the example of FIG. 1, the management device (106) includes a fall prediction monitor (197) for processing a fall prediction assessment. The fall prediction monitor (197) may be configured to receive from a fall prediction controller, a fall prediction assessment of the patient (150) and provide to a user of the management device, information indicative of the fall prediction assessment. For example, information indicative of the fall prediction assessment may include data indicating the likelihood or chance that a particular patient is at risk of falling. The fall prediction monitor (197) may also provide other information about the patient as well, such as data representing location of patient and other indicators (e.g., hydration indicators; gait monitoring indicators; blood pressure indicators; and blood sugar indicators). In a particular embodiment, the fall prediction monitor (197) displays a graphical user interface (GUI) that includes a map with a representation of a patient. In this embodiment, clicking on the representation of the patient, enables a user of the hydration monitor to view indicators associated with the patient as well as a fall prediction assessment of the patient. In a particular embodiment, the fall prediction assessment of the patient may be represented on the GUI as colors. For example, a green color may represent 'patient is at a very low risk of falling', a yellow color may represent 'patient is at a low risk of falling', an orange color may represent 'patient is at a high risk of falling', and a red color may represent 'patient has fallen'.

The management device (106) of FIG. 1 also includes a fall prediction profile generator (198) configured for fall prediction assessment. Specifically, the fall prediction profile generator (198) is configured to identifying, based on health status data associated with the patient, a hydration threshold for the patient. Health status data may be any type of data indicating information about the health or physical condition of the patient. Non-limiting examples of health status data include diagnosis of a medical condition, such as Parkinson's disease; observed, noted, or measured consumption of one or more medications including dosages and types; and observed, noted, or measured physical sensor readings, such as blood pressure measurements, blood sugar level measurements, electrocardiograph (EKG) readings, and many others as will occur to readers of skill in the art. Identifying a hydration threshold based on the health status data may be carried out by identifying an individual hydration threshold one or more of elements contained in the health status data; and selecting the lowest hydration threshold of the individual hydration threshold as the hydration threshold to include in a hydration profile.

For example, a health status data of a patient may include a first element that indicates a diagnosis of low blood pressure and a second element that indicates the patient is consuming a first medication. In this example, the hydration profile generator (198) may identify a first individual hydration threshold of 40 corresponding to the diagnosis of low blood pressure and a second individual hydration threshold of 30 corresponding to the consumption of the first medication. Continuing with this example, the fall prediction profile generator (198) may select the second individual hydration threshold as the hydration threshold to store in the hydration profile for the patient.

Alternatively, the fall prediction profile generator (198) may be configured to store a plurality of thresholds in the hydration profile. For example, the hydration profile may include a second hydration threshold that applies when another indicator of the patient is at a particular level. In this example, the hydration profile may include a second hydration threshold that is used if a fall prediction controller processes a blood sugar indicator that indicates that the patient is experiencing low blood sugar. That is, the hydration profile may include numerous hydration thresholds, each of which is used under particular conditions.

The fall prediction profile generator (198) is also configured to provide the hydration profile to a fall prediction controller to generate a fall prediction assessment of the patient based on the hydration profile and a current hydration indicator associated with the patient. A fall prediction controller may be configured to process indicators associated with a patient and based on those indicators, decide which hydration threshold in the hydration profile to use. For example, if a blood pressure indicator indicates that the patient is currently experiencing normal blood pressure, then the fall prediction controller may be configured to select a first hydration threshold for comparison to a current hydration indicator of the patient. Continuing with this example, if the blood pressure indicator indicates that the patient is currently experiencing low blood pressure then the fall prediction controller may be configured to select a second hydration threshold for comparison to the current hydration indicator of the patient. That is, the fall prediction controller is configured to select from the hydration profile, a hydration threshold that best fits the patient's current health status.

A heath care provider could use a fall prediction assessment to determine when intervention is appropriate for a patient. Providing care for a patient before a fall could save the patient from the considerable cost involved in the treatment and hospitalization of fall injuries and even death.

Figure 2:
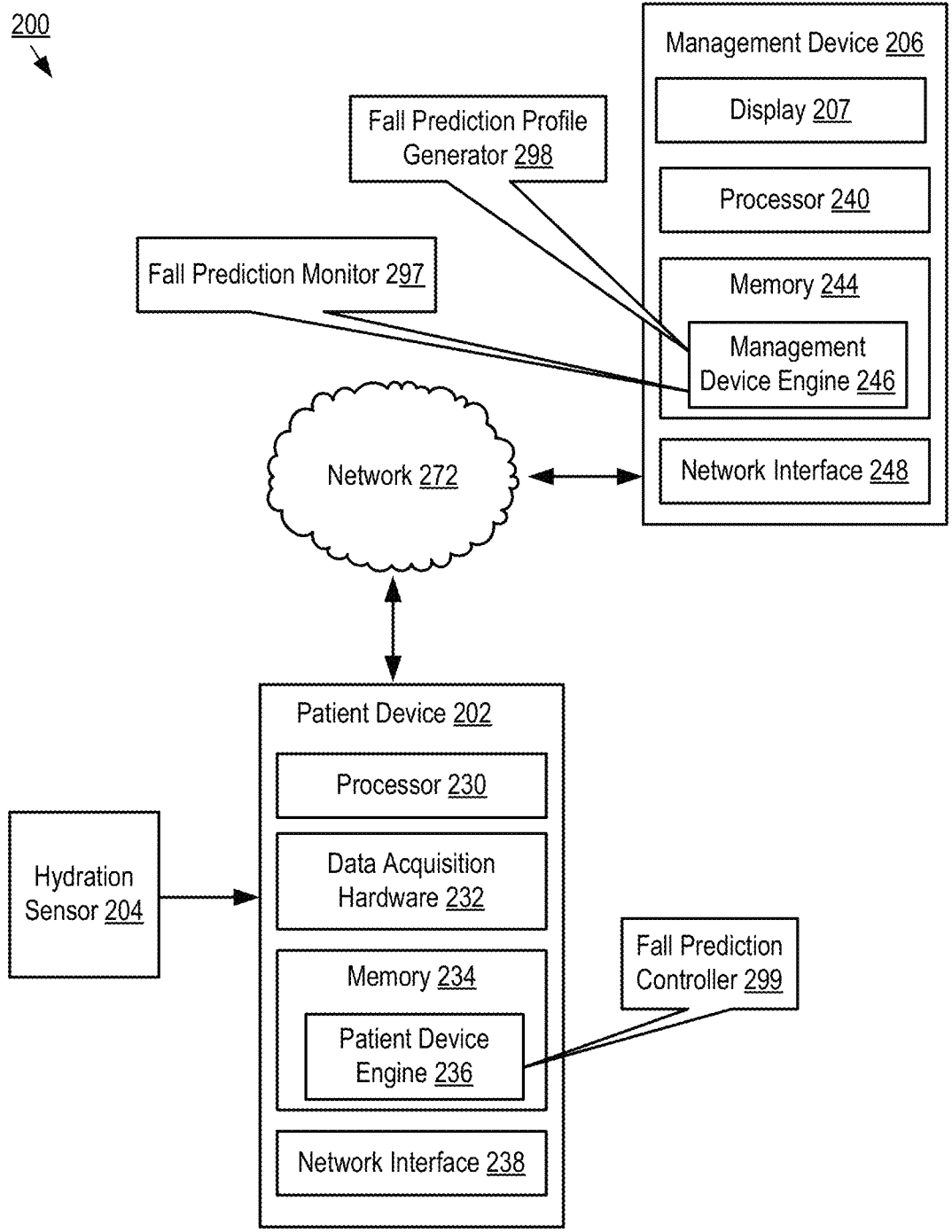
FIG. 2 sets forth a block diagram of another illustrative embodiment of an apparatus that includes a fall prediction controller and a fall prediction profile generator.

Referring to FIG. 2, an illustrative apparatus (200) for fall prediction assessment is shown. The apparatus (200) includes a patient device (202) coupled to a hydration sensor (204) and to a management device (206) via a network (272). As illustrated in FIG. 2, the hydration sensor (204) may be separate from the patient device (202). In some embodiments, the patient device (202) includes the hydration sensor (204).

The patient device (202) includes data acquisition (DAQ) hardware (232) for conversion of the hydration measurement from the hydration sensor (204) to another data form, such as a hydration indicator. The patient device (202) includes a processor (230) and a computer-readable memory, such as memory (234). The memory (234) may include executable code, such as a patient device engine (236).

The patient device engine (236) includes a fall prediction controller (299) comprising automated computing machinery configured to perform a fall prediction assessment. Specifically, the fall prediction controller (299) is configured to compare a hydration indicator to a hydration threshold. A hydration threshold is one or more data values that correspond to a recommended hydration level for a person. A patient having a hydration level that is below the recommended hydration level may be at an increased risk of falling. Comparing the hydration indicator to the hydration threshold may be carried out by determining whether the hydration indicator is below the one or more data values of the hydration threshold and generating a result that indicates whether the hydration indicator is below the one or more data values of the hydration threshold. In a particular embodiment, the result of the comparison is represented as a data value which indicates a difference between the hydration indicator and the hydration threshold. That is, the result of the comparison may represent a severity of separation between the hydration indicator and the hydration threshold.

The fall prediction controller (299) is also configured to generate, based on a result of the comparison of the hydration indicator to the hydration threshold, a fall prediction assessment of the patient. A fall prediction assessment of the patient is an indication of the likelihood that the patient is at risk of falling down, stumbling, or otherwise losing his or her balance.

The patient device (202) also includes a network interface (238), such as an Ethernet port, modem port or other network port adapter. The network interface (238) is adapted to connect to the network (272) and to send the data file to the management device (206) over the network (272). The network (272) may include one or a combination of any type of network such as LAN, WAN, WLAN, public switched telephone network, GSM, or otherwise.

The management device (206) receives the fall prediction assessment and includes a processor (240) and a computer-readable memory, such as memory (244). The management device (206) also includes a display (207) for displaying information related to fall prediction assessment. The memory (244) can store the fall prediction assessment and includes computer-executable code, such as a management engine (246). The management engine (246) may periodically, such as once per minute, scan data files stored in the memory (244) to determine whether new or additional data is in the memory (244). In some embodiments, the management engine (246) can format the data file into various forms and notify pre-determined authorized persons on a user list stored in the memory (244), such as by electronic mail, that a new data file is present and ready for review. Formatting the data file may include sorting the data into a database, generating a waveform, and creating a visual display of the data, such as by creating a jpeg file.

The management device (206) also includes a fall prediction monitor (297) for processing a fall prediction assessment. The fall prediction monitor (297) may be configured to receive from the fall prediction controller (299), a fall prediction assessment of the patient and provide to a user of the management device (206), information indicative of the fall prediction assessment. For example, information indicative of the fall prediction assessment may include data indicating the likelihood or chance that a particular patient is at risk of falling. The fall prediction monitor (297) may also provide other information about the patient as well, such as data representing location of patient and other indicators (e.g., hydration indicators; gait monitoring indicators; blood pressure indicators; and blood sugar indicators).

The management device (206) of FIG. 1 also includes a fall prediction profile generator (298) configured for fall prediction assessment. Specifically, the fall prediction profile generator (298) is configured to identifying, based on health status data associated with the patient, a hydration threshold for the patient. Health status data may be any type of data indicating information about the health or physical condition of the patient. The fall prediction profile generator (298) is also configured to store the identified hydration threshold as part of a hydration profile associated with the patient. The fall prediction profile generator (298) is also configured to provide the hydration profile to the fall prediction controller (299) to generate a fall prediction assessment of the patient based on the hydration profile and a current hydration indicator associated with the patient.

Physicians or authorized persons may use the management device (206) to access the data file and/or formatted data in the management device memory (244). For example, a separate device may access a web interface that authenticates the separate device users and allows the users to view the fall prediction assessments or any other function associated with viewing, managing, and analyzing the fall prediction assessments. Accordingly, embodiments of the present invention allow patients to stay at home while the management device (206) monitors signals from the patient device (202) and provides medical personnel in a remote location with access to the fall prediction assessments.

In some embodiments of the present invention, the patient device (202) may be remotely configured or updated from the management device (206) through the network (272). For example, additional software, software updates, and fall prediction profiles may be sent over the network (272) and installed onto the patient device (202) using a device connected to, and communicating through, the network (272).

In some embodiments of the present invention, the patient device memory (234) may store the hydration measurements, hydration indicators, results of comparisons, hydration thresholds, hydration profiles, and fall prediction assessments. The patient device (202) may be in communication with a data storage system, directly or through a local network, to store the sensor data and/or data file. For example, if the network (272) failed, the patient device memory (234) and/or data storage system may provide a back-up storage to data stored on the management device (206).

Figure 3:
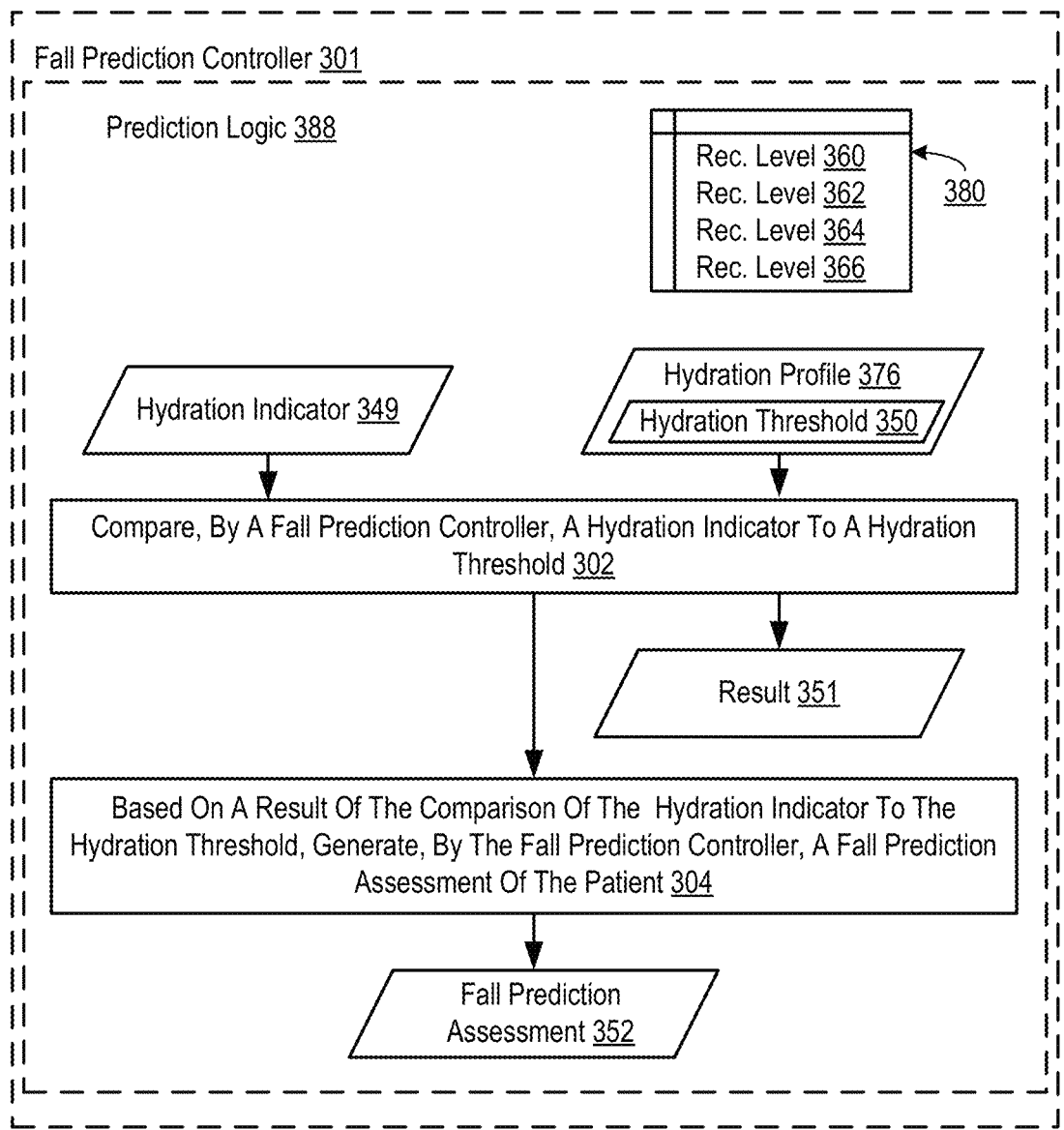
FIG. 3 sets forth a flow chart illustrating an illustrative embodiment of a method for fall prediction assessment.
Figure 3:
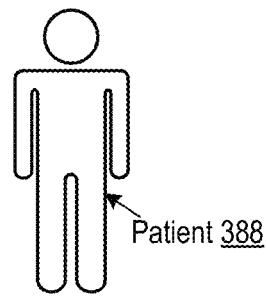

For further explanation, FIG. 3 sets forth a flow chart illustrating an illustrative embodiment of a method for fall prediction assessment. The method of FIG. 3 includes a fall prediction controller (301) that includes prediction logic (388) for comparing (302) a hydration indicator (349) to a hydration threshold (350). The hydration indicator (350) corresponds to a hydration level of a patient. Comparing (302) a hydration indicator (349) to a hydration threshold (350) may be carried out by determining whether the hydration indicator is below the one or more data values of the hydration threshold and generating a result that indicates whether the hydration indicator is below the one or more data values of the hydration threshold. In a particular embodiment, the result of the comparison is represented as a data value which indicates a difference between the hydration indicator and the hydration threshold. That is, the result of the comparison may represent a severity of separation between the hydration indicator and the hydration threshold.

The method of FIG. 3 includes the fall prediction controller (301) generating (304), based on a result (351) of the comparison of the hydration indicator (349) to the hydration threshold (350), a fall prediction assessment (352) of the patient (388). A fall prediction assessment of the patient (388) is an indication of the likelihood that the patient is at risk of falling down, stumbling, or otherwise losing his or her balance. A fall prediction assessment may be a simple binary data value, where a '0' represents 'patient is not at risk of falling' and a '1' represents 'patient is at risk of falling'. The fall prediction assessment may also indicate one or more values with a range of possible values where each value has a different risk level associated with it. As a non-limiting example, a '0' data value for the fall prediction assessment may represent 'patient is at a low risk of falling', a '1' may represent 'patient is at a medium risk of falling', a '2' may represent 'patient is a high risk of falling', and a '3' may represent "patient is at a very high risk of falling". Generating (304), based on a result (351) of the comparison of the hydration indicator (349) to the hydration threshold (350), a fall prediction assessment (352) of the patient (388) may be carried out by corresponding to the result of the comparison a data value representing the fall prediction assessment.

As explained above, a hydration threshold may be specified in a hydration profile corresponding to the patient. In a particular embodiment, the hydration threshold (350) corresponds to a minimum recommended hydration level (360) for a patient consuming a particular type of medication. Specific types of medications may increase a risk of a patient falling. Non-limiting examples of medications that may increase a patient falling include serotonin-reuptake inhibitors, tricyclic antidepressants, neuroleptic agents, benzodiazapines, anticonvulsants, and class IA antiarrhythmic medications, and many others as will occur to those of readers of skill in the art. In a particular embodiment, the hydration threshold (350) of the hydration profile (376) corresponds to a minimum recommended hydration level (362) for a patient consuming a specific combination of two or more types of medications. In a particular embodiment, the hydration threshold (350) of the hydration profile (376) corresponds to a minimum recommended hydration level (364) for a patient having a particular medical condition. In a particular embodiment, the hydration threshold (350) of the hydration profile (376) corresponds to a minimum recommended hydration level (366) for a patient having a particular medical condition and consuming a particular medication. The recommended hydration levels may be stored in a recommended hydration level table (380).

Figure 4:
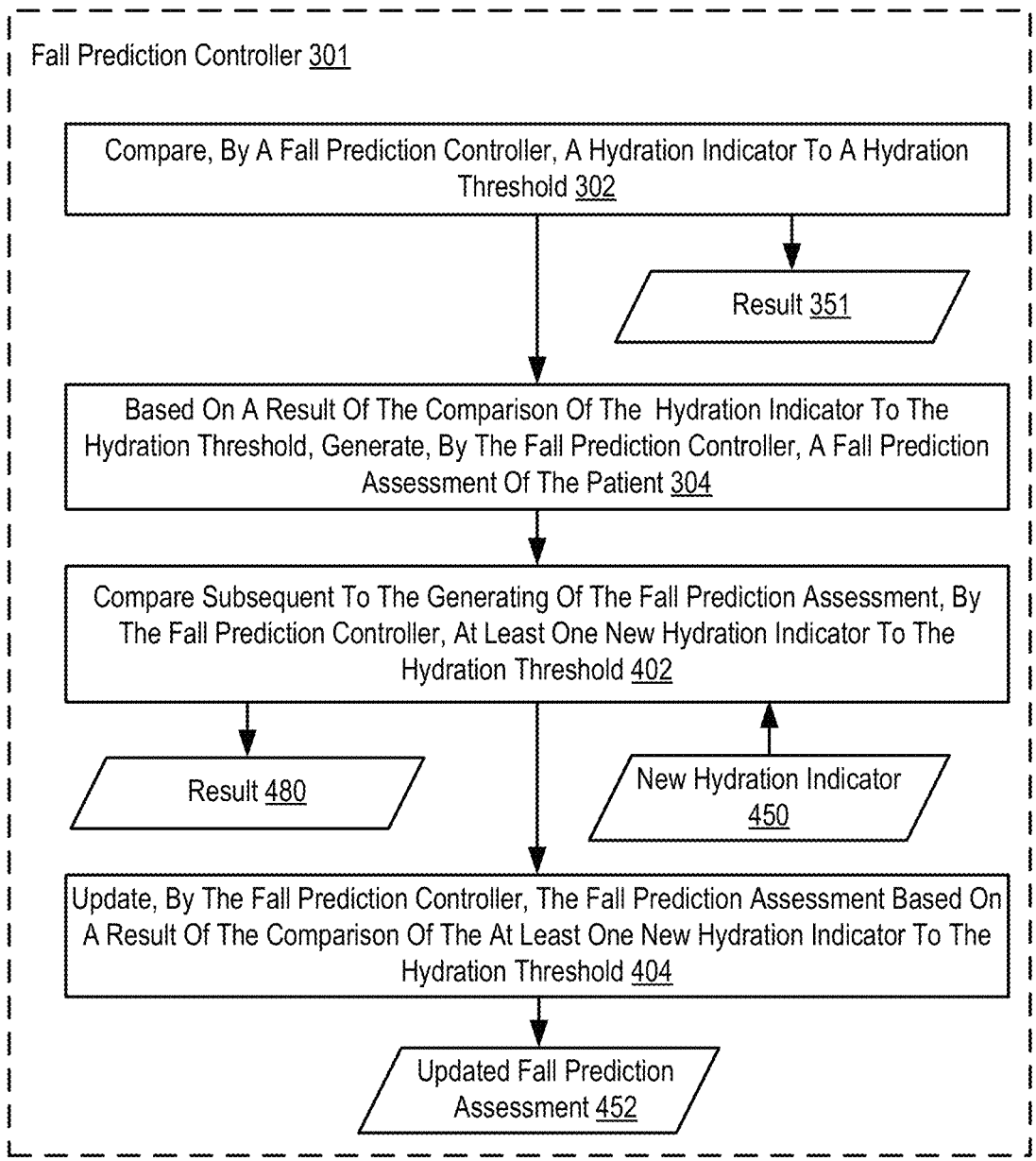
FIG. 4 sets forth a flow chart illustrating another illustrative embodiment of a method for fall prediction assessment.

For further explanation, FIG. 4 sets forth a flow chart illustrating another illustrative embodiment of a method for fall prediction assessment. The method of FIG. 4 is similar to the method of FIG. 3 in that the method of FIG. 4 also includes a fall prediction controller (301) comparing (302) a hydration indicator (349) to a hydration threshold (350) and generating (304), based on a result (351) of the comparison of the hydration indicator (349) to the hydration threshold (350), a fall prediction assessment (352) of the patient (388).

The method of FIG. 4 also includes the fall prediction controller (301) comparing (402) subsequent to the generating (304) of the fall prediction assessment (352) at least one new hydration indicator (450) to the hydration threshold (350). Comparing (402) subsequent to the generating (304) of the fall prediction assessment (352) at least one new hydration indicator (450) to the hydration threshold (350) may be carried out by determining whether the hydration indicator is below the one or more data values of the hydration threshold and generating a result that indicates whether the hydration indicator is below the one or more data values of the hydration threshold.

The method of FIG. 4 also includes the fall prediction controller (301) updating (404), based on a result (480) of the comparison of the at least one new hydration indicator (450) to the hydration threshold (350), the fall prediction assessment (352). Updating (404), based on a result (480) of the comparison of the at least one new hydration indicator (450) to the hydration threshold (350), the fall prediction assessment (352) may be carried out by corresponding to the result of the comparison a data value representing the fall prediction assessment.

Figure 5:
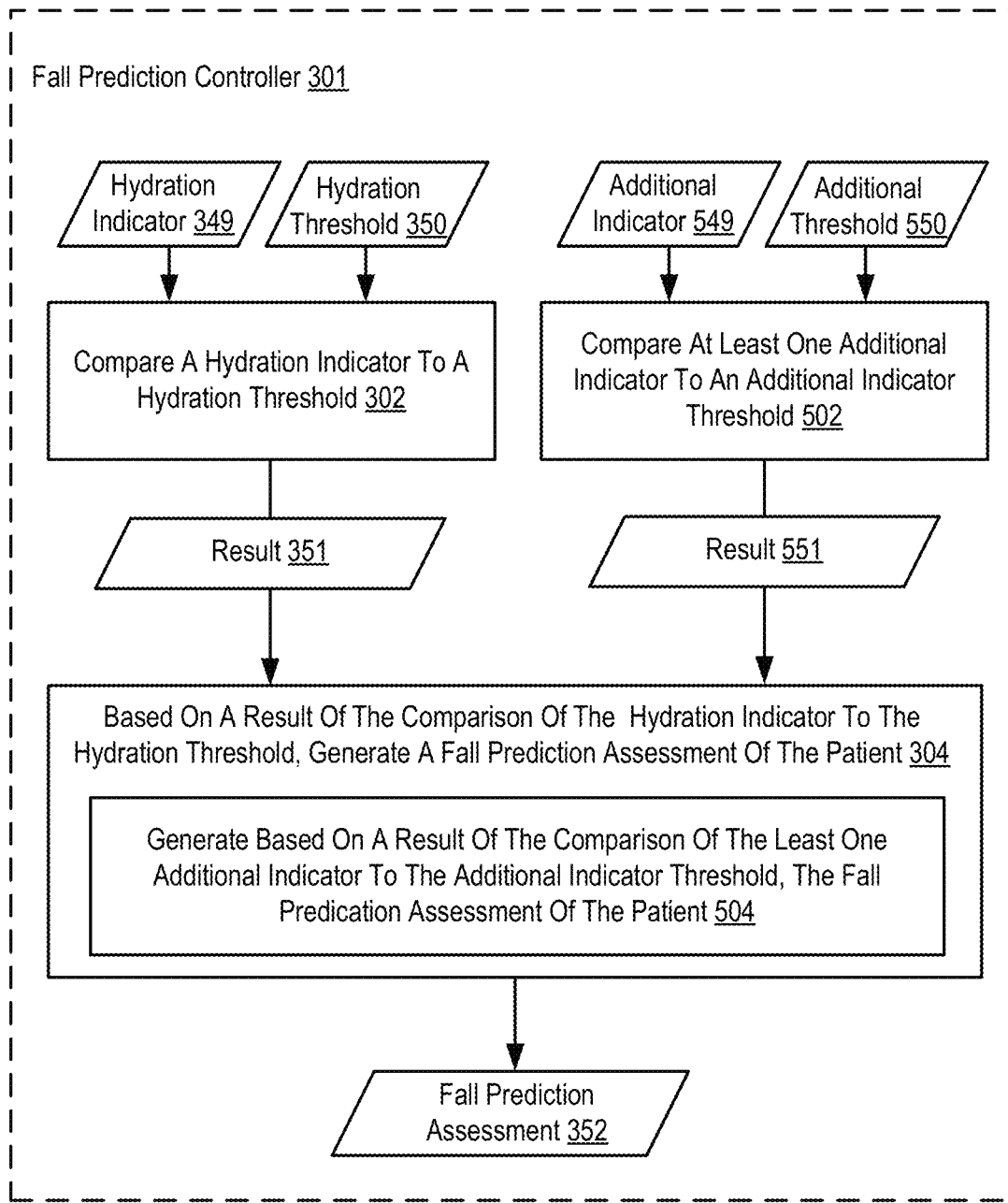
FIG. 5 sets forth a flow chart illustrating another illustrative embodiment of a method for fall prediction assessment.

For further explanation, FIG. 5 sets forth a flow chart illustrating another illustrative embodiment of a method for fall prediction assessment. The method of FIG. 5 is similar to the method of FIG. 3 in that the method of FIG. 5 also includes a fall prediction controller (301) comparing (302) a hydration indicator (349) to a hydration threshold (350) and generating (304), based on a result (351) of the comparison of the hydration indicator (349) to the hydration threshold (350), a fall prediction assessment (352) of the patient (388).

The method of FIG. 5 includes the fall prediction controller (301) comparing (502) at least one additional indicator (549) to an additional indicator threshold (550). Non-limiting examples of additional indicators include a gait monitoring indicator; a blood sugar indicator; a blood pressure indicator, and many others as will occur to readers of skill in the art. Comparing (502) at least one additional indicator (549) to an additional indicator threshold (550) may be carried out by determining whether the indicator is below the one or more data values of the threshold and generating a result that indicates whether the indicator is below the one or more data values of the threshold.

In the method of FIG. 5, generating (304), based on a result (351) of the comparison of the hydration indicator (349) to the hydration threshold (350), a fall prediction assessment (352) of the patient (388) includes generating (504), based on a result (551) of the comparison of the at least one additional indicator (549) to the additional indicator threshold (550). Generating (504), based on a result (551) of the comparison of the at least one additional indicator (549) to the additional indicator threshold (550), a fall prediction assessment (352) of the patient (388) may be carried out by corresponding to the result of the comparison a data value representing the fall prediction assessment.

Figure 6:
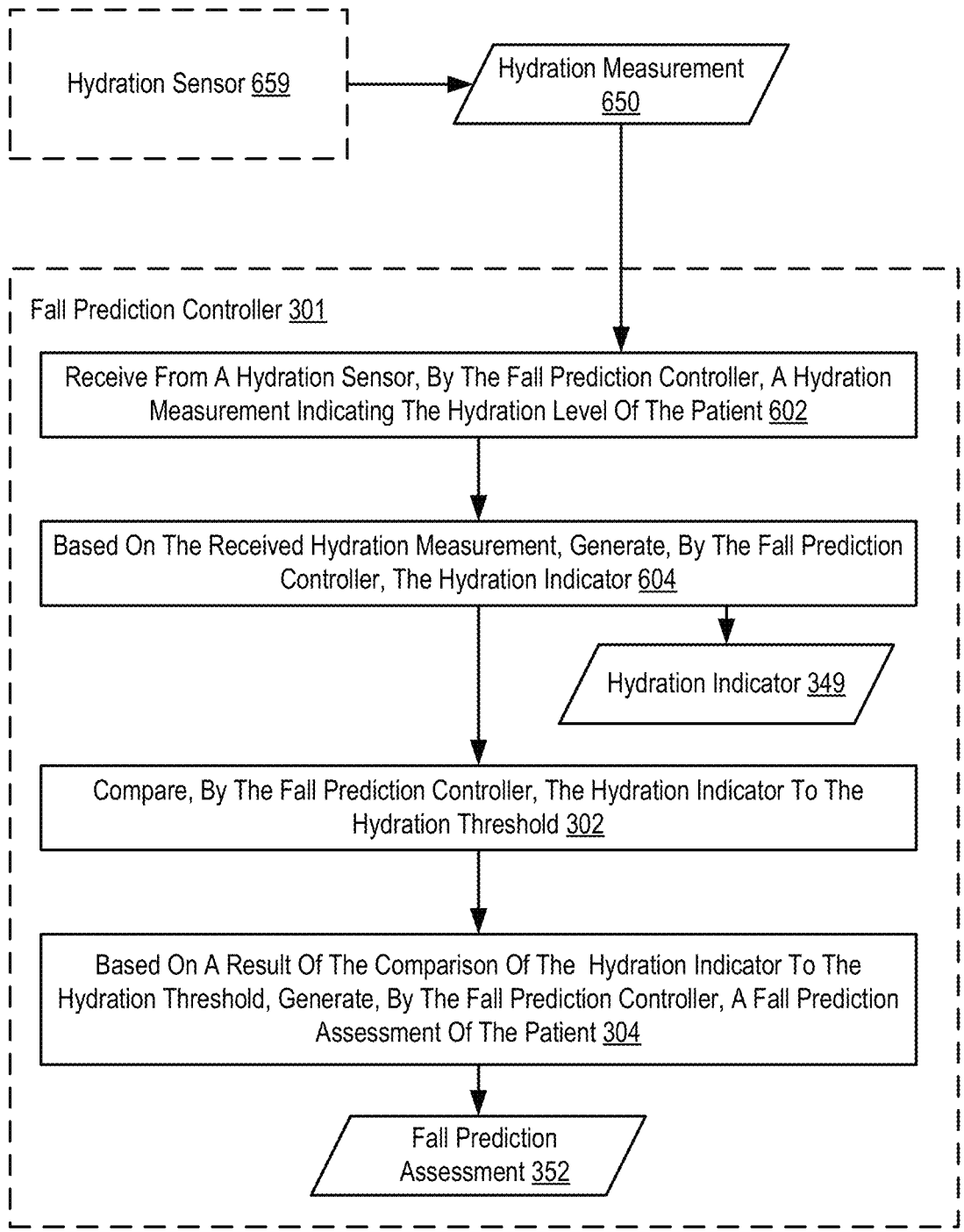
FIG. 6 sets forth a flow chart illustrating another illustrative embodiment of a method for fall prediction assessment.

For further explanation, FIG. 6 sets forth a flow chart illustrating another illustrative embodiment of a method for fall prediction assessment. The method of FIG. 6 is similar to the method of FIG. 3 in that the method of FIG. 6 also includes a fall prediction controller (301) comparing (302) a hydration indicator (349) to a hydration threshold (350) and generating (304), based on a result (351) of the comparison of the hydration indicator (349) to the hydration threshold (350), a fall prediction assessment (352) of the patient (388).

The method of FIG. 6 includes the fall prediction controller (301) receiving (602) from a hydration sensor (659), a hydration measurement (650) indicating the hydration level of the patient (388). Receiving (602) from a hydration sensor (659), a hydration measurement (650) indicating the hydration level of the patient (388) may be carried out by periodically polling or receiving hydration measurements from the hydration sensor (659) by monitoring the existence and strength of a signal from the hydration sensor (659).

The method of FIG. 6 also includes the fall prediction controller (301) generating (604), based on the received hydration measurement (650), the hydration indicator (349). Generating (604), based on the received hydration measurement (650), the hydration indicator (349) may be carried out by converting the format of the received hydration measurement to a hydration indicator.

Figure 7:
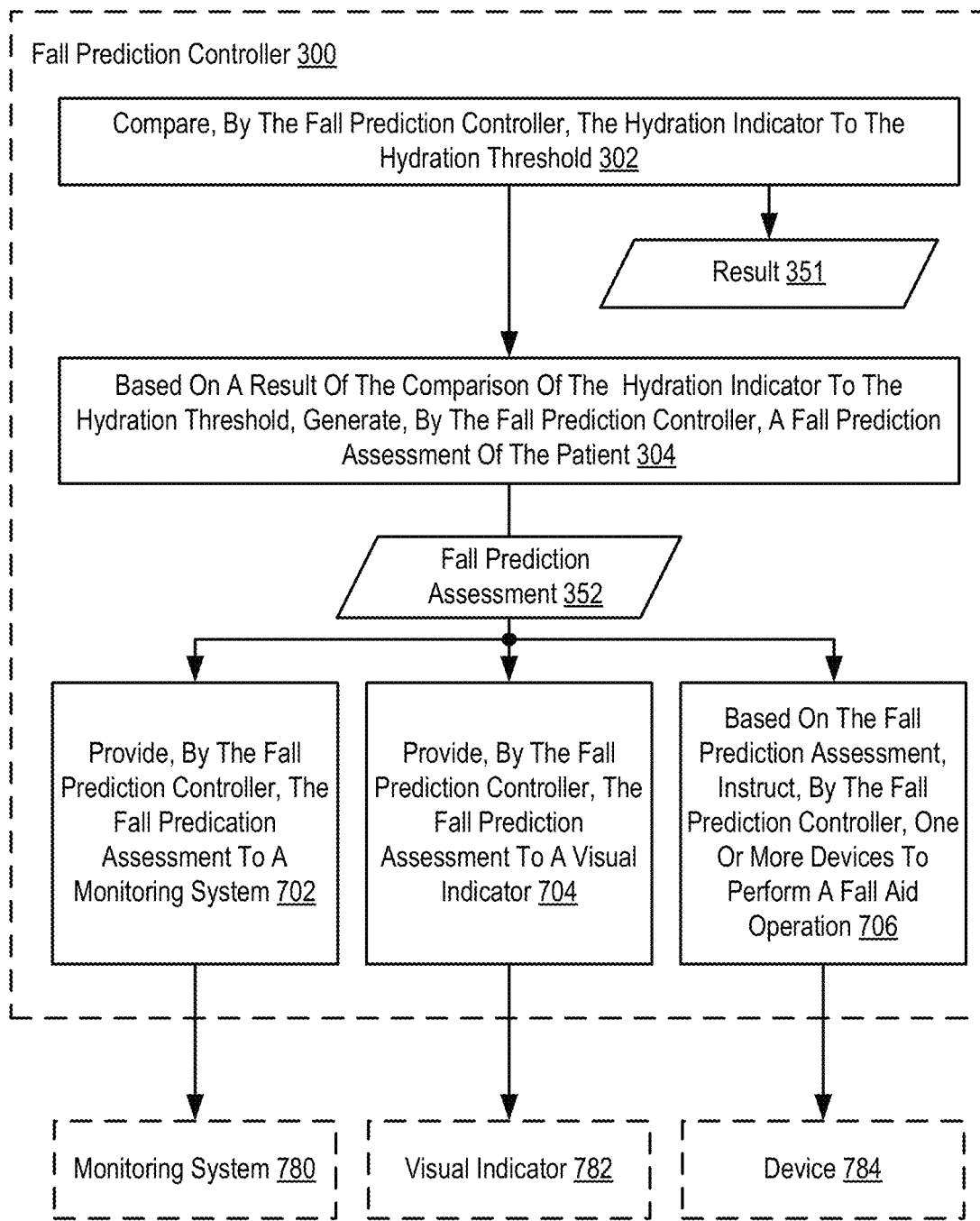
FIG. 7 sets forth a flow chart illustrating another illustrative embodiment of a method for fall prediction assessment.

For further explanation, FIG. 7 sets forth a flow chart illustrating another illustrative embodiment of a method for fall prediction assessment. The method of FIG. 7 is similar to the method of FIG. 3 in that the method of FIG. 7 also includes a fall prediction controller (301) comparing (302) a hydration indicator (349) to a hydration threshold (350) and generating (304), based on a result (351) of the comparison of the hydration indicator (349) to the hydration threshold (350), a fall prediction assessment (352) of the patient (388).

The method of FIG. 7 optionally includes the fall prediction controller (301) providing (702) the fall prediction assessment (352) to a monitoring system (780). Providing (702) the fall prediction assessment (352) to a monitoring system (780) may be carried out by transmitting the fall prediction assessment to a fall prediction monitor, such as the fall prediction monitor (197) of FIG. 1.

The method of FIG. 7 optionally includes the fall prediction controller (301) providing (704) the fall prediction assessment (352) to a visual indicator (782). Providing (704) the fall prediction assessment (352) to a visual display (782) may be carried out by transmitting information indicative of the fall prediction assessment to a display device, such as the display (207) of FIG. 2.

The method of FIG. 7 also optionally includes the fall prediction controller (301) instructing (706), based on the fall prediction assessment (352), one or more devices (784) to perform a fall aid operation. For example, the fall prediction controller (199) may send an instruction to access device (179) to perform a fall aid operation. A fall aid operation may be any type of action that assists in fall prevention, detection, or response of the patient. Non-limiting examples of fall aid operations include unlocking doors to a car, room, house, or building; turning on lights in a room; sounding one or more audible alarms or paying recorded instructions to the patient via a speaker; turning on a room intercom that connects the patient with a personal health care provider, such as a nursing attendant; and turning on a video camera that provides current video images of the patient to personal health care provider.

Figure 8:
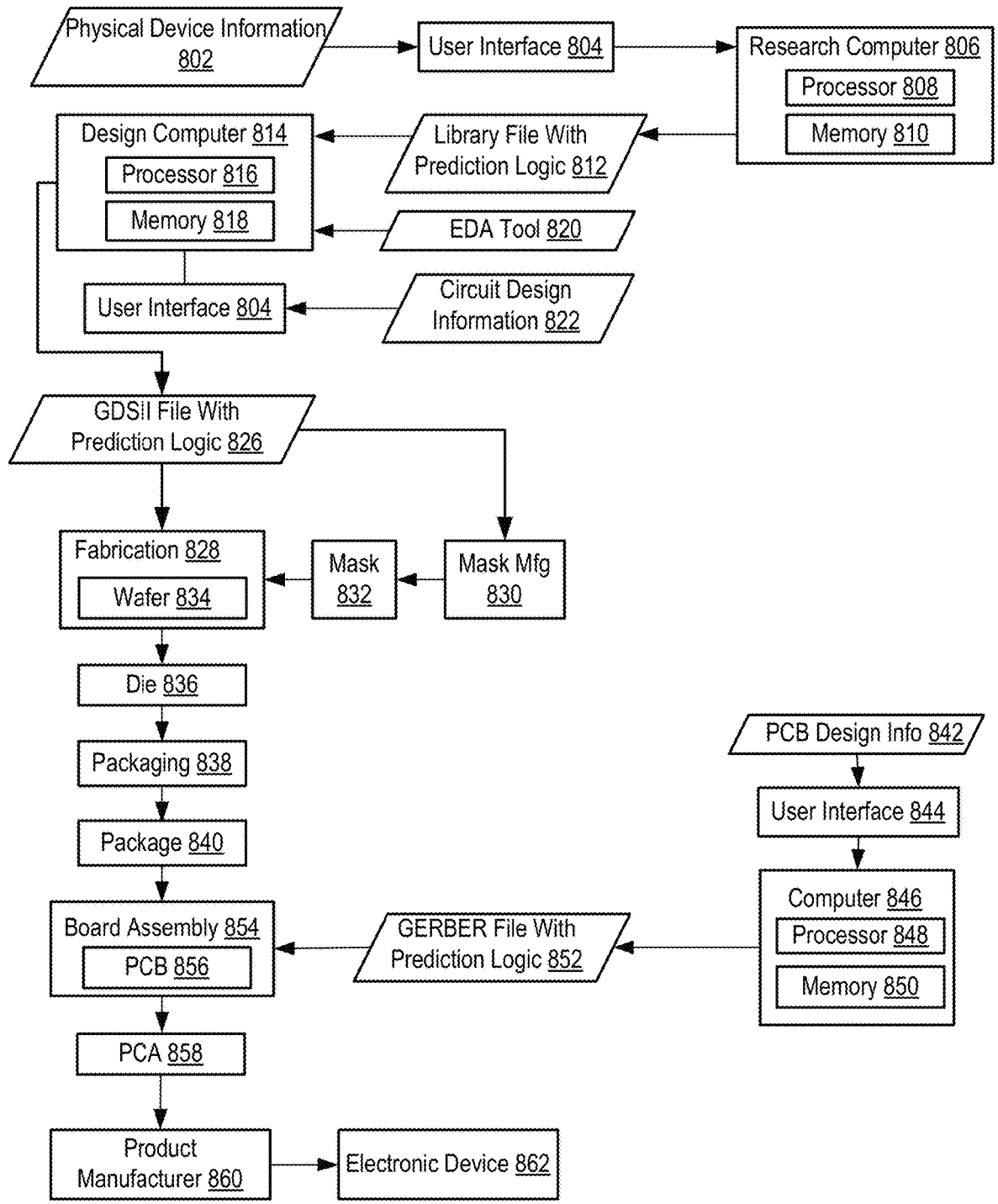
FIG. 8 sets forth a data flow diagram illustrating a manufacturing process for a device that includes a fall prediction controller.

For further explanation, FIG. 8 sets forth a data flow diagram illustrating a manufacturing process (800) for a device that includes a fall prediction controller. Physical device information (802 is received at the manufacturing process (800), such as at a research computer (806). The physical device information (802) may include design information representing at least one physical property of a semiconductor device, such as a device that includes the fall prediction controller (199) of FIG. 1 (e.g., the patient device (102) of FIG. 1), a device that includes the fall prediction controller (299) of FIG. 2 (e.g., the patient device (202) of FIG. 2), a device that includes the fall prediction controller (301) of FIGS. 3-7, or any combination thereof. For example, the physical device information (802) may include physical parameters, material characteristics, and structure information that is entered via a user interface (804) coupled to the research computer (806). The research computer (806) includes a processor (808), such as one or more processing cores, coupled to a computer readable medium such as a memory (810). The memory (810) may store computer readable instructions that are executable to cause the processor (808) to transform the physical device information (802) to comply with a file format and to generate a library file (812).

In a particular embodiment, the library file (812) includes at least one data file including the transformed design information. For example, the library file (812) may include a library of semiconductor devices including a device that includes the fall prediction controller (199) of FIG. 1 (e.g., the patient device (102) of FIG. 1), a device that includes the fall prediction controller (299) of FIG. 2 (e.g., the patient device (202) of FIG. 2), a device that includes the fall prediction controller (301) of FIGS. 3-7, or any combination thereof, that is provided to use with an electronic design automation (EDA) tool (820).

The library file (812) may be used in conjunction with the EDA tool (820) at a design computer (814) including a processor (816), such as one or more processing cores, coupled to a memory (818). The EDA tool (820) may be stored as processor executable instructions at the memory (818) to enable a user of the design computer (814) to design a circuit including a device that includes the fall prediction controller (199) of FIG. 1 (e.g., the patient device (102) of FIG. 1), a device that includes the fall prediction controller (299) of FIG. 2 (e.g., the patient device (202) of FIG. 2), a device that includes the fall prediction controller (301) of FIGS. 3-7, or any combination thereof, of the library file (812). For example, a user of the design computer (814) may enter circuit design information (822) via a user interface (824) coupled to the design computer (814). The circuit design information (822) may include design information representing at least one physical property of a semiconductor device, such as a device that includes the fall prediction controller (199) of FIG. 1 (e.g., the patient device (102) of FIG. 1), a device that includes the fall prediction controller (299) of FIG. 2 (e.g., the patient device (202) of FIG. 2), a device that includes the fall prediction controller (301) of FIGS. 3-7, or any combination thereof. To illustrate, the circuit design property may include identification of particular circuits and relationships to other elements in a circuit design, positioning information, feature size information, interconnection information, or other information representing a physical property of a semiconductor device.

The design computer (814) may be configured to transform the design information, including the circuit design information (822), to comply with a file format. To illustrate, the file formation may include a database binary file format representing planar geometric shapes, text labels, and other information about a circuit layout in a hierarchical format, such as a Graphic Data System (GDSII) file format. The design computer (814) may be configured to generate a data file including the transformed design information, such as a GDSII file (826) that includes information describing a device that includes the fall prediction controller (199) of FIG. 1 (e.g., the patient device (102) of FIG. 1), a device that includes the fall prediction controller (299) of FIG. 2 (e.g., the patient device (202) of FIG. 2), a device that includes the fall prediction controller (301) of FIGS. 3-7, or any combination thereof, in addition to other circuits or information. To illustrate, the data file may include information corresponding to a system-on-chip (SOC) that includes a device that includes the fall prediction controller (199) of FIG. 1 (e.g., the patient device (102) of FIG. 1), a device that includes the fall prediction controller (299) of FIG. 2 (e.g., the patient device (202) of FIG. 2), a device that includes the fall prediction controller (301) of FIGS. 3-7, or any combination thereof and that also includes additional electronic circuits and components within the SOC.

The GDSII file (826) may be received at a fabrication process (828) to manufacture a device that includes the fall prediction controller (199) of FIG. 1 (e.g., the patient device (102) of FIG. 1), a device that includes the fall prediction controller (299) of FIG. 2 (e.g., the patient device (202) of FIG. 2), a device that includes the fall prediction controller (301) of FIGS. 3-7, or any combination thereof, according to transformed information in the GDSII file (826). For example, a device manufacture process may include providing the GDSII file (826) to a mask manufacturer (830) to create one or more masks, such as masks to be used with photolithography processing, illustrated as a representative mask (832). The mask (832) may be used during the fabrication process to generate one or more wafers (834), which may be tested and separated into dies, such as a representative die (836). The die (836) includes a circuit including a device that includes the fall prediction controller (199) of FIG. 1 (e.g., the patient device (102) of FIG. 1), a device that includes the fall prediction controller (299) of FIG. 2 (e.g., the patient device (202) of FIG. 2), a device that includes the fall prediction controller (301) of FIGS. 3-7, or any combination thereof.

The die (836) may be provided to a packaging process (838) where the die (836) is incorporated into a representative package (840). For example, the package (840) may include the single die (836) or multiple dies, such as a system-in-package (SiP) arrangement. The package (840) may be configured to conform to one or more standards or specifications, such as Joint Electron Device Engineering Council (JEDEC) standards.

Information regarding the package (840) may be distributed to various product designers, such as via a component library stored at a computer (846). The computer (846) may include a processor (848), such as one or more processing cores, coupled to a memory (850). A printed circuit board (PCB) tool may be stored as processor executable instructions at the memory (850) to process PCB design information (842) received from a user of the computer (846) via a user interface (844). The PCB design information (842) may include physical positioning information of a packaged semiconductor device on a circuit board, the packaged semiconductor device corresponding to the package (840) including a device that includes the fall prediction controller (199) of FIG. 1 (e.g., the patient device (102) of FIG. 1), a device that includes the fall prediction controller (299) of FIG. 2 (e.g., the patient device (202) of FIG. 2), a device that includes the fall prediction controller (301) of FIGS. 3-7, or any combination thereof.

The computer (846) may be configured to transform the PCB design information (842) to generate a data file, such as a GERBER file (852) with data that includes physical positioning information of a packaged semiconductor device on a circuit board, as well as layout of electrical connections such as traces and vias, where the packaged semiconductor device corresponds to the package (840) including the fall prediction controller (199) of FIG. 1, the fall prediction controller (299) of FIG. 2, the fall prediction controller (301) of FIGS. 3-7, or any combination thereof. In other embodiments, the data file generated by the transformed PCB design information may have a format other than a GERBER format.

The GERBER file (852) may be received at a board assembly process (854) and used to create PCBs, such as a representative PCB (856), manufactured in accordance with the design information stored within the GERBER file (852). For example, the GERBER file (852) may be uploaded to one or more machines to perform various steps of a PCB production process. The PCB (856) may be populated with electronic components including the package (840) to form a representative printed circuit assembly (PCA) (858).

The PCA (858) may be received at a product manufacture process (860) and integrated into one or more electronic devices, such as a first representative electronic device (862) and a second representative electronic device (864). As an illustrative, non-limiting example, the first representative electronic device (862), the second representative electronic device (864), or both, may be selected from the group of a set top box, a music player, a video player, an entertainment unit, a navigation device, a communications device, a personal digital assistant (PDA), a fixed location data unit, and a computer, into which the at least one controllable energy consuming module is integrated. As another illustrative, non-limiting example, one or more of the electronic devices (862) and (864) may be remote units such as mobile phones, hand-held personal communication systems (PCS) units, portable data units such as personal data assistants, global positioning system (GPS) enabled devices, navigation devices, fixed location data units such as meter reading equipment, or any other device that stores or retrieves data or computer instructions, or any combination thereof. Although FIG. 8 illustrates remote units according to teachings of the disclosure, the disclosure is not limited to these exemplary illustrated units. Embodiments of the disclosure may be suitably employed in any device which includes active integrated circuitry including memory and on-chip circuitry.

A device that includes the fall prediction controller (199) of FIG. 1, the fall prediction controller (299) of FIG. 2, the fall prediction controller (301) of FIGS. 3-7, or any combination thereof, may be fabricated, processed, and incorporated into an electronic device, as described in the illustrative process (800). One or more aspects of the embodiments disclosed with respect to FIGS. 1-7 may be included at various processing stages, such as within the library file (812), the GDSII file (826), and the GERBER file (852), as well as stored at the memory (810) of the research computer (806), the memory (818) of the design computer (814), the memory (850) of the computer (846), the memory of one or more other computers or processors (not shown) used at the various stages, such as at the board assembly process (854), and also incorporated into one or more other physical embodiments such as the mask (832), the die (836), the package (840), the PCA (858), other products such as prototype circuits or devices (not shown), or any combination thereof. For example, the GDSII file (826) or the fabrication process (828) can include a computer readable tangible medium storing instructions executable by a computer, the instructions including instructions that are executed by the computer to perform the methods of FIGS. 3-7, or any combination thereof. Although various representative stages of production from a physical device design to a final product are depicted, in other embodiments fewer stages may be used or additional stages may be included. Similarly, the process (800) may be performed by a single entity, or by one or more entities performing various stages of the process (800).

Figure 9:
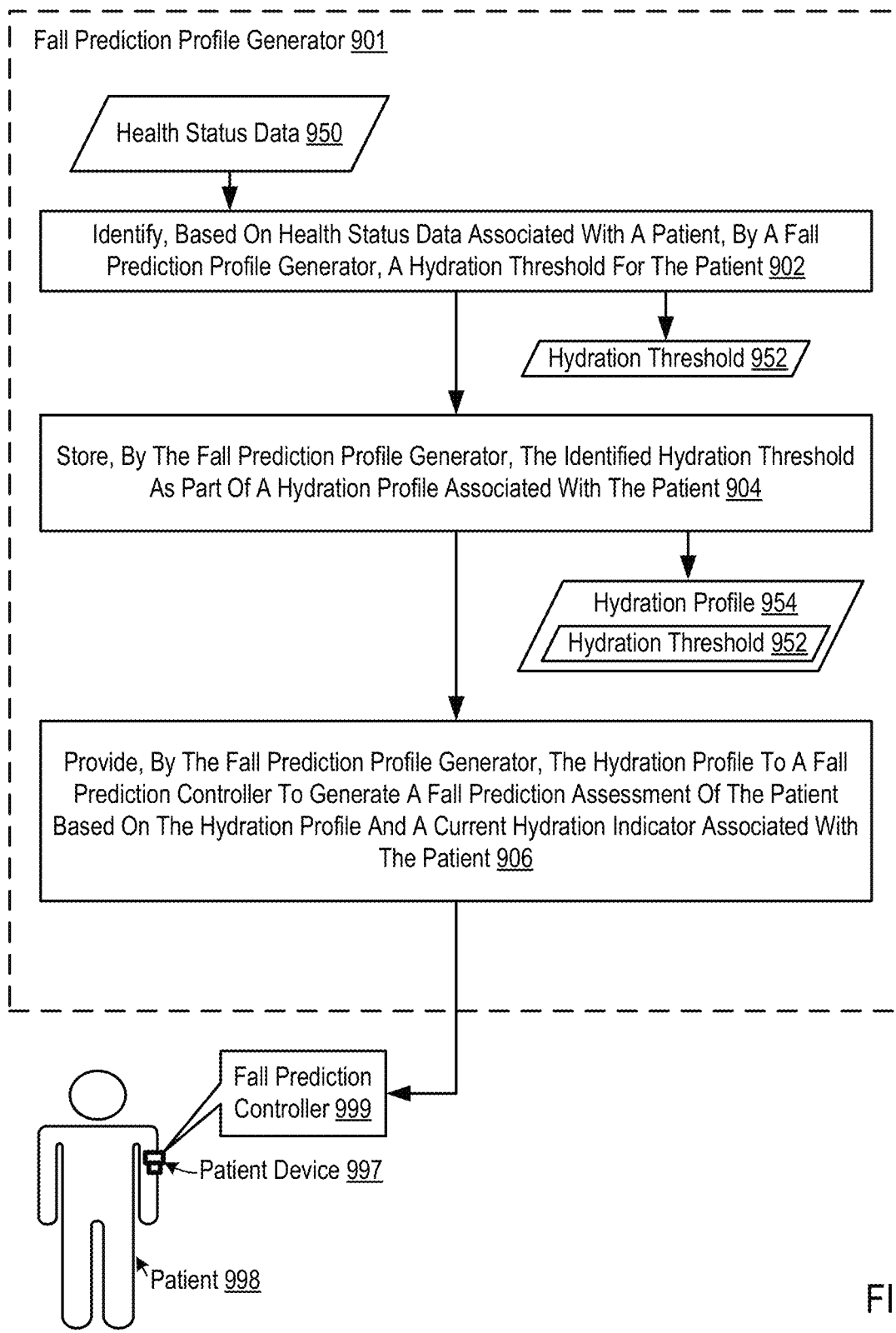
FIG. 9 sets forth a flow chart illustrating another illustrative embodiment of a method for fall prediction assessment.

For further explanation, FIG. 9 sets forth a flow chart illustrating another illustrative embodiment of a method for fall prediction assessment. The method of FIG. 9 includes a fall prediction profile generator (901) identifying (902), based on health status data (950) associated with a patient (998), a hydration threshold (952) for the patient (998). Identifying, based on health status data associated with the patient, a hydration threshold for the patient. Health status data may be any type of data indicating information about the health or physical condition of the patient. Non-limiting examples of health status data include diagnosis of a medical condition, such as a disease; observed, noted, or measured consumption of one or more medications including dosages and types; and observed, noted, or measured physical sensor readings, such as blood pressure measurements, blood sugar level measurements, electrocardiograph (EKG) readings, and many others as will occur to readers of skill in the art. Identifying (902), based on health status data (950) associated with a patient (998), a hydration threshold (952) for the patient (998) may be carried out by identifying an individual hydration threshold one or more of elements contained in the health status data; and selecting the lowest hydration threshold of the individual hydration threshold as the hydration threshold to include in a hydration profile.

For example, health status data of a patient may include a first element that indicates a diagnosis of low blood pressure and a second element that indicates the patient is consuming a first medication. In this example, the hydration profile generator (901) may identify a first individual hydration threshold of 40 corresponding to the diagnosis of low blood pressure and a second individual hydration threshold of 30 corresponding to the consumption of the first medication. Continuing with this example, the fall prediction profile generator (901) may select the second individual hydration threshold as the hydration threshold to store in the hydration profile for the patient.

The method of FIG. 9 also includes the fall prediction profile generator (901) storing (904) the identified hydration threshold (952) as part of a hydration profile (954) associated with the patient (998). The hydration profile may include a plurality of thresholds in addition to the hydration threshold. For example, the hydration profile may include a second hydration threshold that applies when another indicator of the patient is at a particular level. In this example, the hydration profile may include a second hydration threshold that is used if a fall prediction controller processes a blood sugar indicator that indicates that the patient is experiencing low blood sugar. That is, the hydration profile may include numerous hydration thresholds, each of which is used under particular conditions. Storing (904) the identified hydration threshold (952) as part of a hydration profile (954) associated with the patient (998) may be carried out by recording data into memory within a management device.

The method of FIG. 9 also includes the fall prediction profile generator (901) providing (906) the hydration profile (954) to a fall prediction controller (999) to generate a fall prediction assessment of the patient (998) based on the hydration profile (954) and a current hydration indicator associated with the patient (998). Providing (906) the hydration profile (954) to a fall prediction controller (999) may be carried out by transmitting the hydration profile to the fall prediction controller via a data communications network.

Figure 10:
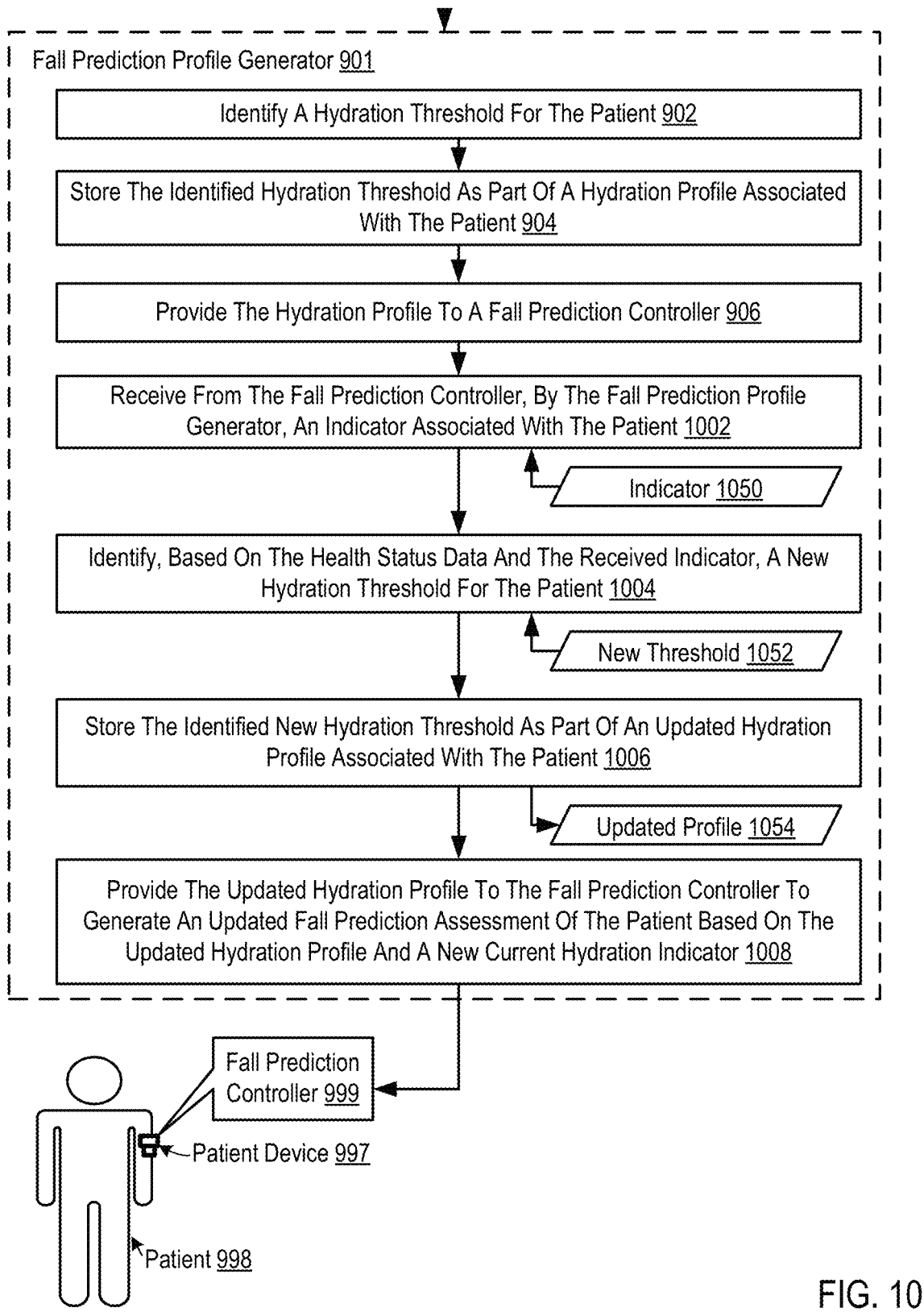
FIG. 10 sets forth a flow chart illustrating another illustrative embodiment of a method for fall prediction assessment.

For further explanation, FIG. 10 sets forth a flow chart illustrating another illustrative embodiment of a method for fall prediction assessment. The method of FIG. 10 is similar to the method of FIG. 9 in that the method of FIG. 10 also includes identifying (902), based on health status data (950) associated with a patient (998), a hydration threshold (952) for the patient (998); storing (904) the identified hydration threshold (952) as part of a hydration profile (954) associated with the patient (998); and providing (906) the hydration profile (954) to a fall prediction controller (999) to generate a fall prediction assessment of the patient (998) based on the hydration profile (954) and a current hydration indicator associated with the patient (998).

The method of FIG. 10 also includes the fall prediction controller (901) receiving (1002) from the fall prediction controller (999), an indicator (1050) associated with the patient (998). Non-limiting examples of indicators include gait monitoring indicators; blood pressure indicators; and blood sugar level indicators. Receiving from the fall prediction controller (999), an indicator (1050) associated with the patient (998) may be carried out by receiving data from the fall prediction controller via a data communication network.

The method of FIG. 10 also includes the fall prediction controller (901) identifying (1004), based on the health status data (950) and the received indicator (1050), a new hydration threshold (1052) for the patient (998). Identifying (1004), based on the health status data (950) and the received indicator (1050), a new hydration threshold (1052) for the patient (998) may be carried out by identifying an individual hydration threshold one or more of elements contained in the health status data; and selecting the lowest hydration threshold of the individual hydration threshold as the hydration threshold to include in a hydration profile.

The method of FIG. 10 also includes the fall prediction controller (901) storing (1006) the identified new hydration threshold (1052) as part of an updated hydration profile (1054) associated with the patient (998). Storing (1006) the identified new hydration threshold (1052) as part of an updated hydration profile (1054) associated with the patient (998) may be carried out by adding one or more data values to the hydration profile.

The method of FIG. 10 also includes the fall prediction controller (901) providing (1008) the updated hydration profile (1054) to the fall prediction controller (999) to generate an updated fall prediction assessment of the patient (999) based on the updated hydration profile (1054) and a new current hydration indicator associated with the patient (998). Providing (1008) the updated hydration profile (1054) to the fall prediction controller (999) may be carried out by transmitting the hydration profile to the fall prediction controller via a data communications network.

Figure 11:
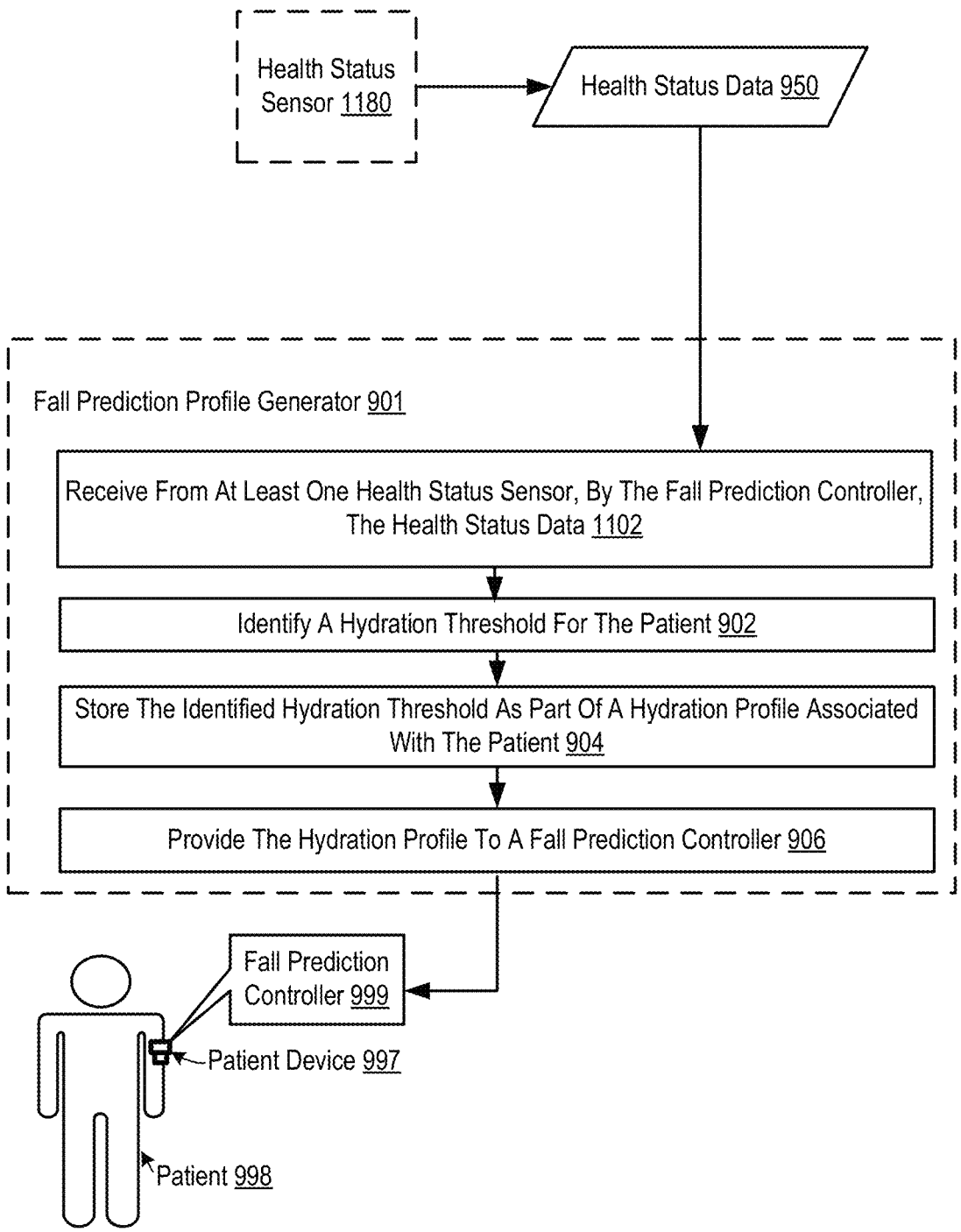
FIG. 11 sets forth a flow chart illustrating another illustrative embodiment of a method for fall prediction assessment.

For further explanation, FIG. 11 sets forth a flow chart illustrating another illustrative embodiment of a method for fall prediction assessment. The method of FIG. 11 is similar to the method of FIG. 9 in that the method of FIG. 11 also includes identifying (902), based on health status data (950) associated with a patient (998), a hydration threshold (952) for the patient (998); storing (904) the identified hydration threshold (952) as part of a hydration profile (954) associated with the patient (998); and providing (906) the hydration profile (954) to a fall prediction controller (999) to generate a fall prediction assessment of the patient (998) based on the hydration profile (954) and a current hydration indicator associated with the patient (998).

The method of FIG. 11 also includes the fall prediction profile generator (901) receiving (1102) from at least one health status sensor (1180), the health status data (950). Non-limiting examples of health status data include diagnosis of a medical condition, such as a disease; observed, noted, or measured consumption of one or more medications including dosages and types; and observed, noted, or measured physical sensor readings, such as blood pressure measurements, blood sugar level measurements, electrocardiograph (EKG) readings, and many others as will occur to readers of skill in the art. Receiving (1102) from at least one health status sensor (1180), the health status data (950) may be carried out by receiving one or more elements of data through a data communications network.

Figure 12:
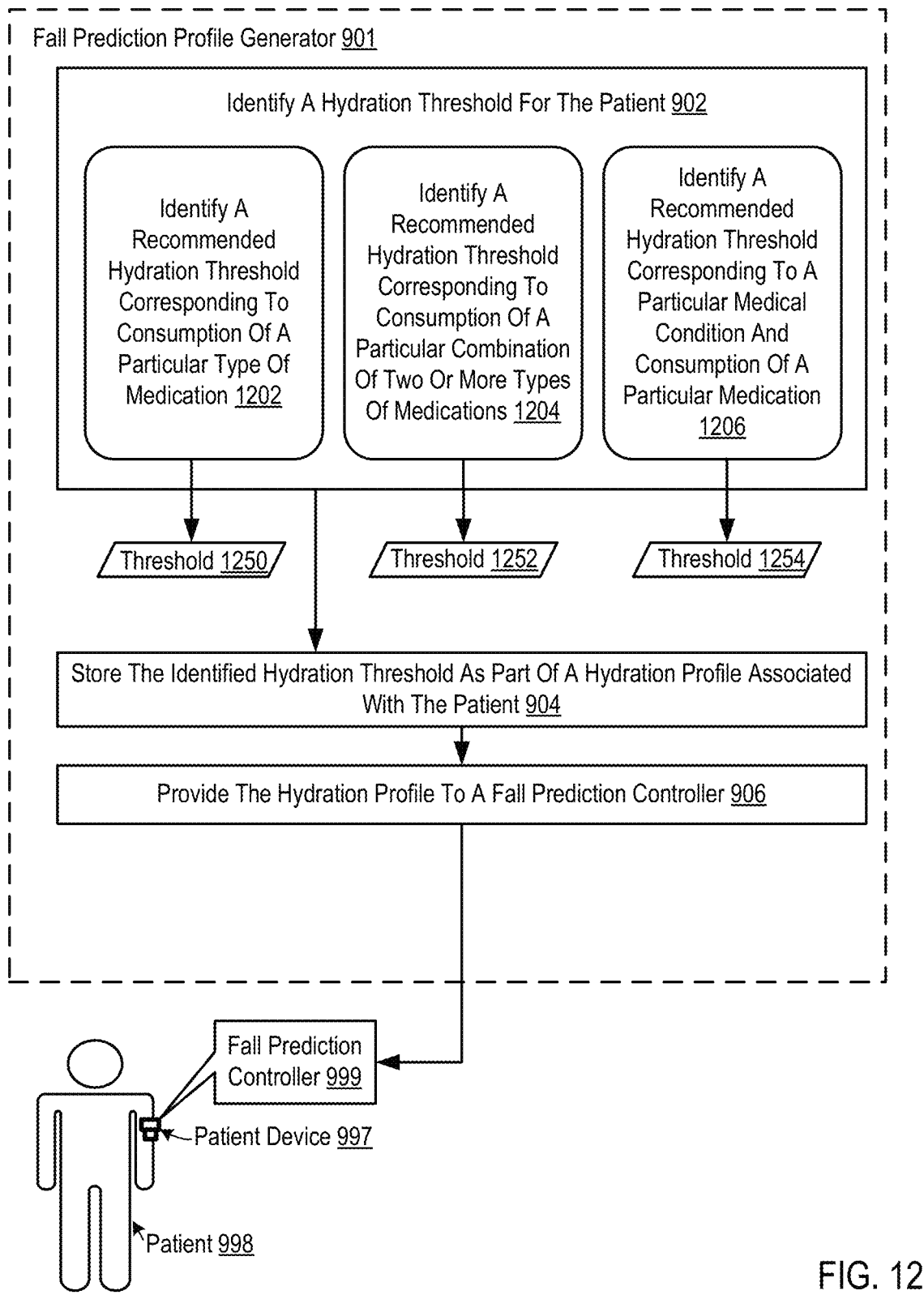
FIG. 12 sets forth a flow chart illustrating another illustrative embodiment of a method for fall prediction assessment.

For further explanation, FIG. 12 sets forth a flow chart illustrating another illustrative embodiment of a method for fall prediction assessment. The method of FIG. 12 is similar to the method of FIG. 9 in that the method of FIG. 12 also includes identifying (902), based on health status data (950) associated with a patient (998), a hydration threshold (952) for the patient (998); storing (904) the identified hydration threshold (952) as part of a hydration profile (954) associated with the patient (998); and providing (906) the hydration profile (954) to a fall prediction controller (999) to generate a fall prediction assessment of the patient (998) based on the hydration profile (954) and a current hydration indicator associated with the patient (998).

In the method of FIG. 12, identifying (902), based on health status data (950) associated with a patient (998), a hydration threshold (952) for the patient (998) optionally includes identifying (1202) a recommended hydration threshold (1250) corresponding to consumption of a particular type of medication. Specific types of medications may increase a risk of a patient falling. Non-limiting examples of medications that may increase a patient falling include serotonin-reuptake inhibitors, tricyclic antidepressants, neuroleptic agents, benzodiazapines, anticonvulsants, and class IA antiarrhythmic medications, and many others as will occur to those of readers of skill in the art. Identifying (1202) a recommended hydration threshold (1250) corresponding to consumption of a particular type of medication may be carried out by identifying an individual hydration threshold one or more of elements contained in the health status data.

In the method of FIG. 12, identifying (902), based on health status data (950) associated with a patient (998), a hydration threshold (952) for the patient (998) optionally includes identifying (1204) a recommended hydration threshold (1252) corresponding to consumption of the particular combination of two or more types of medications. Identifying (1204) a recommended hydration threshold (1252) corresponding to consumption of the particular combination of two or more types of medications may be carried out by identifying an individual hydration threshold one or more of elements contained in the health status data.

In the method of FIG. 12, identifying (902), based on health status data (950) associated with a patient (998), a hydration threshold (952) for the patient (998) optionally includes identifying (1206) a recommended hydration threshold (1254) corresponding to the particular medical condition and consumption of the particular medication. Identifying (902), based on health status data (950) associated with a patient (998), a hydration threshold (952) for the patient (998) optionally includes identifying (1206) a recommended hydration threshold (1254) corresponding to the particular medical condition and consumption of the particular medication may be carried out by identifying an individual hydration threshold one or more of elements contained in the health status data.

Those of skill would further appreciate that the various illustrative logical blocks, configurations, modules, circuits, and method steps described in connection with the embodiments disclosed herein may be implemented as electronic hardware, computer software executed by a processing unit, or combinations of both. Various illustrative components, blocks, configurations, modules, circuits, and steps have been described above generally in terms of their functionality. Whether such functionality is implemented as hardware or executable processing instructions depends on the particular application and design constraints imposed on the overall system. Skilled artisans may implement the described functionality in varying ways with each particular application, but such implementation decisions should not be interpreted as causing a departure from the scope of the present disclosure.

The steps of a method or algorithm described in connection with the embodiments disclosed herein may be embodied directly in hardware, in a software module executed by a processor, or in a combination of the two. A software module may reside in random access memory (RAM), a magnetoresistive random access memory (MRAM), a spin-torque-transfer MRAM (STT-MRAM), flash memory, read-only memory (ROM), programmable read-only memory (PROM), erasable programmable read-only memory (EPROM), electrically erasable programmable read-only memory (EEPROM), registers, hard disk, a removable disk, a compact disc read-only memory (CD-ROM), or any other form of storage medium known in the art. An exemplary storage medium is coupled to the processor such that the processor can read information from, and write information to, the storage medium. In the alternative, the storage medium may be integral to the processor. The processor and the storage medium may reside in an application-specific integrated circuit (ASIC). The ASIC may reside in a computing device or a user terminal. In the alternative, the processor and the storage medium may reside as discrete components in a computing device or user terminal.

The previous description of the disclosed embodiments is provided to enable any person skilled in the art to make or use the disclosed embodiments. Various modifications to these embodiments will be readily apparent to those skilled in the art, and the principles defined herein may be applied to other embodiments without departing from the scope of the disclosure. Thus, the present disclosure is not intended to be limited to the embodiments shown herein but is to be accorded the widest scope possible consistent with the principles and novel features as defined by the following claims.

What is claimed is:

1. A method for initiating a remote intervention to prevent a patient from falling based on digitized patient health data and measured hydration level data, the method comprising:
receiving, by a processing system from a wearable device configured to be worn by a patient, health status data associated with the patient, wherein the processing system and the wearable device communicate over one or more networks, the health status data including one or more indicators of the patient's health or physical condition, and one or more data points associated with the one or more indicators;
calculating, by the processing system, hydration thresholds for the one or more indicators included in the received health status data, including a hydration threshold associated with one or more data points associated with the one or more indicators;
creating, by the processing system, a patient hydration profile associating calculated hydration thresholds with relevant patient health status data;
storing, by the processing system, the patient hydration profile associated with the patient; and
providing, by the processing system over the one or more networks, the hydration profile to a fall prediction controller of the wearable device to predict the likelihood that the patient will fall based on the patient's hydration profile, the patient health status data, and the patient's measured hydration levels.

2. The method of claim 1 wherein the health status data associated with the patient indicates whether the patient consumes a particular combination of two or more types of medications; wherein identifying the hydration threshold for the patient includes identifying a hydration threshold corresponding to consumption of the particular combination of two or more types of medications.

3. The method of claim 1 wherein the health status data associated with the patient indicates whether the patient has a particular medical condition and consumes a particular medication; wherein identifying the hydration threshold for the patient includes identifying a hydration threshold corresponding to the particular medical condition and consumption of the particular medication.

4. The method of claim 1 wherein the patient hydration profile comprises one or more thresholds, each threshold corresponding to at least one indicator of a patient's health.

5. The method of claim 1, wherein the patient hydration profile comprises one threshold, the threshold corresponding to two or more indicators of a patient's health.

6. The method of claim 1, wherein an indicator of the patient's health comprises one or more of the following: the patient's blood pressure, the patient's blood sugar, the patient's electrocardiograph (EKG) readings, diagnosis of a medical condition, and observed, noted, or measured consumption, by the patient, of one or more medications including dosages and types.

7. The method of claim 1, wherein a data point associated with an indicator includes a measurement associated with the indicator.

8. An apparatus for initiating a remote intervention to prevent a patient from falling based on digitized patient health data and measured hydration level data, the apparatus comprising a computer processor and computer memory operatively coupled to the computer processor, the computer memory having disposed within it computer program instructions that, when executed by the computer processor, cause the apparatus to carry out the steps of:
receiving, by a processing system from a wearable device configured to be worn by a patient, health status data associated with the patient, wherein the processing system and the wearable device communicate over one or more networks, the health status data including one or more indicators of the patient's health or physical condition, and one or more data points associated with the one or more indicators;
calculating, by the processing system, hydration thresholds for the one or more indicators included in the received health status data, including a threshold associated with one or more data points associated with the one or more indicators;
creating, by the processing system, a patient hydration profile associating calculated hydration thresholds with relevant patient health status data;
storing, by the processing system, the patient hydration profile associated with the patient; and
providing, by the processing system over the one or more networks, the hydration profile to a fall prediction controller of the wearable device to predict the likelihood that the patient will fall based on the patient's hydration profile, the patient health data, and the patient's measured hydration levels, and a current hydration indicator associated with the patient.

9. The apparatus of claim 8 wherein the health status data associated with the patient indicates whether the patient consumes a particular combination of two or more types of medications; wherein identifying the hydration threshold for the patient includes identifying a hydration threshold corresponding to consumption of the particular combination of two or more types of medications.

10. The apparatus of claim 8 wherein the health status data associated with the patient indicates whether the patient has a particular medical condition and consumes a particular medication; wherein identifying the hydration threshold for the patient includes identifying a hydration threshold corresponding to the particular medical condition and consumption of the particular medication.

11. The apparatus of claim 8, wherein the patient hydration profile comprises one or more thresholds, each threshold corresponding to at least one indicator of a patient's health.

12. The apparatus of claim 8, wherein the patient hydration profile comprises one threshold, the threshold corresponding to two or more indicators of a patient's health.

13. The apparatus of claim 8, wherein an indicator of the patient's health comprises one or more of the following: the patient's blood pressure, the patient's blood sugar, the patient's electrocardiograph (EKG) readings, diagnosis of a medical condition, and observed, noted, or measured consumption, by the patient, of one or more medications including dosages and types.

14. The apparatus of claim 8, wherein a data point associated with an indicator includes a measurement associated with the indicator.

15. A computer readable storage medium storing instructions executable by a computer for initiating a remote intervention to prevent a patient from falling based on digitized patient health data and measured hydration level data received from a wearable device over one or more networks, the wearable device configured to be worn by the patient, the instructions comprising:
instructions that when executed by the computer cause the computer to analyze, by the processing system, health status data associated with a patient, the health status data including one or more indicators of the patient's health or physical condition, and one or more data points associated with the one or more indicators;

instructions that when executed by the computer cause the computer to calculate, by the processing system, hydration thresholds for the one or more indicators included in the received health status data, including a hydration threshold associated with one or more data points associated with the one or more indicators;

instructions that when executed by the computer cause the computer to create, by the processing system, a patient hydration profile associating calculated hydration thresholds with relevant patient health status data;

instructions that when executed by the computer cause the computer to store, by the processing system, the patient hydration threshold as part of a hydration profile associated with the patient;

instructions that when executed by the computer cause the computer to provide, by the processing system over the one or more networks, the hydration profile to a fall prediction controller of the wearable device to predict a likelihood that the patient will fall based on the patient's hydration profile, the patient health data, and the patient's measured hydration levels.

16. The computer readable storage medium of claim 15 wherein the health status data associated with the patient indicates whether the patient consumes a particular combination of two or more types of medications; wherein identifying the hydration threshold for the patient includes identifying a hydration threshold corresponding to consumption of the particular combination of two or more types of medications.

17. The computer readable storage medium of claim 15 wherein the health status data associated with the patient indicates whether the patient has a particular medical condition and consumes a particular medication; wherein identifying the hydration threshold for the patient includes identifying a hydration threshold corresponding to the particular medical condition and consumption of the particular medication.

* * * * *